United States Patent [19]

Sorensen et al.

[11] 4,116,336

[45] Sep. 26, 1978

[54] PACKAGE CONTAINING A REFERENCE LIQUID FOR BLOOD GAS EQUIPMENT

[75] Inventors: Søren Kaj Sørensen, Glostrup; Carl Christian Holbek, Allerød, both of Denmark

[73] Assignee: Radiometer A/S, Copenhagen, Denmark

[21] Appl. No.: 773,222

[22] Filed: Mar. 1, 1977

Related U.S. Application Data

[63] Continuation-in-part of Ser. No. 652,817, Jan. 27, 1976, abandoned.

[30] Foreign Application Priority Data

May 30, 1975 [DK] Denmark ............................. 2449/75
Jun. 17, 1976 [DK] Denmark ............................. 2724/76

[51] Int. Cl.$^2$ ..................... C09K 3/00; B65B 31/00; B65D 81/20; B65D 85/70
[52] U.S. Cl. ..................... 206/524.8; 23/230 B; 23/232 R; 422/61; 206/0.6; 206/0.7; 206/524.2; 252/408; 424/2; 424/3; 53/408
[58] Field of Search ....... 252/408; 23/230 B, 253 TP, 23/253 R, 232 R, 254 R; 424/2, 3; 206/0.6, 0.7, 524.8, 210, 524.2; 53/22 B, , 7, 12; 222/3, 4

[56] References Cited

U.S. PATENT DOCUMENTS

| 1,970,193 | 8/1934 | Riebel, Jr. ............................. 53/22 B |
| 3,380,929 | 4/1968 | Petersen ................................ 252/408 |
| 3,615,709 | 10/1971 | Ford et al. ............................ 206/0.6 |
| 3,681,255 | 8/1972 | Wilfore .................................. 252/408 |
| 3,859,049 | 1/1975 | Ware et al. ........................... 23/230 B |
| 3,864,084 | 2/1975 | Folkman ............................... 23/230 B |
| 3,874,850 | 4/1975 | Sorensen et al. ................... 23/230 B |
| 3,892,058 | 7/1975 | Komatsu et al. ...................... 53/22 B |
| 3,922,363 | 11/1975 | Mitsuda et al. ........................ 53/22 B |
| 3,922,473 | 11/1975 | Kosaka et al. ......................... 252/408 |

FOREIGN PATENT DOCUMENTS

| 2,236,909 | 2/1974 | Fed. Rep. of Germany ........... 252/408 |
| 1,444,713 | 8/1976 | United Kingdom .................... 53/22 B |
| 1,343,870 | 1/1974 | United Kingdom ..................... 252/408 |

OTHER PUBLICATIONS

Clark, L. C. et al., Ala. J. Med. Sci., vol. 9, No. 1, pp. 16-29 (1972).

Primary Examiner—Benjamin R. Padgett
Assistant Examiner—T. S. Gron
Attorney, Agent, or Firm—Hubbell, Cohen, Stiefel & Gross

[57] ABSTRACT

A package containing a reference liquid for the calibration and/or quality control of blood gas analyzers. The reference liquid is enclosed in a flexible, gas-tight container without any gas bubbles in the container, and to avoid any danger of formation of gas bubbles, the total gas pressure in the liquid is kept below 600 mm Hg at 37° C. The container is preferably a laminate bag of aluminum foil with interior layer of heat sealable plastic of low gas permeability, preferably a polyacrylonitrile copolymer.

14 Claims, 5 Drawing Figures

PACKAGE CONTAINING A REFERENCE LIQUID FOR BLOOD GAS EQUIPMENT

CROSS-REFERENCE TO RELATED APPLICATION

This application is a continuation-in-part of application Ser. No. 652,817, filed Jan. 27, 1976, now abandoned.

FIELD OF THE INVENTION

The present invention relates to a package containing a reference liquid for quality control and/or calibration of blood gas measuring equipment.

BACKGROUND OF THE INVENTION

Blood gas measuring apparatuses are known which are designed for measuring, by means of suitable measuring electrodes, blood pH, concentration of dissolved carbon dioxide in blood, expressed as $P_{CO_2}$ (the partial pressure of carbon dioxide) and the concentration of dissolved oxygen in the blood, expressed as $P_{O_2}$ (the partial pressure of oxygen), and one known fully automatic blood gas measuring apparatus (Radiometer ABL1, described, e.g. in U.S. Pat. No. 3,874,850) also simultaneously measures the blood hemoglobin content (Hb) which is otherwise normally measured separately.

From these four central parameters may be calculated various derived parameters which are of great significance to the judgement of so-called acid-base status of the organism.

The measurements referred to above are all relative measurements where the unknown sample is compared with standards. Hence, the quality of these standards is decisive to the quality of the measurement of the single parameters.

When using manual or semiautomatic blood gas measuring equipment, great technical skill is nowadays a requirement to the user of the measuring equipment in order to obtain measurements of satisfactory quality. The technical level of the user may be lower when a fully automatic self-calibrating equipment is used, e.g. of the type described in the above-mentioned U.S. Pat. No. 3,874,850, but this does not remove the necessity or desirability of being able to check the measuring quality of the equipment, including the quality of the standards, calibration liquids, etc., of the equipment, using a known reference.

Even though it is, in principle, generally known to check a measuring equipment by introducing a sample of known properties into the equipment, this is a great problem in connection with equipment for measuring pH - $P_{CO_2}$ - $P_{O_2}$ - and optionally Hb.

A sample (a blood sample or another aqueous solution) of this type is normally not stable during any longer period ($CO_2$ and $O_2$ escape from the sample) which means that the sample must be prepared on the spot by the user. Normally, this gives rise to problems involving extraordinarily much labor, expensive extra equipment and uncertainty, as the preparation process is technically rather complicated.

All over the world, there is in our days an interest in a control system for measuring values from equipment of the type mentioned, as this equipment is used directly in connection with patient treatment and often under extremely critical circumstances (e.g. during surgery).

In the U.S.A., Congress has dealt with this problem during recent years, and at present, the legislation tends toward requiring that the "supplier of blood data", e.g. the head doctor of the laboratory, shall be able to prove, at any time, that the measuring equipment used is able to yield reliable data in that it has been checked by means of a system independent of the normal calibration system of the equipment (quality control).

Hence, the general desire to-day (also outside the U.S.A.) is that one would be able to buy for this quality control, small containers with samples of known composition and of great reliability.

All blood gas measuring equipment commercially available requires frequent calibration, usually with intervals of some hours. For this purpose, the known art uses, for certain types of equipment, various calibration liquids, some of which (e.g. pH buffer mixtures) are commercially available in small containers and show high reliability with respect to keeping the stated pH values, whereas the calibration liquids for the calibration of other parts of the measuring equipment, e.g. the $P_{CO_2}$ measuring equipment and the $P_{O_2}$ measuring equipment, are at the moment not commercially available in easily handled packages. Some technically advanced blood gas analyzers, e.g. the above-mentioned fully automatic Radiometer ABL1 gas measuring equipment, use solutions which in the equipment proper are equilibrated with known gas mixtures to obtain well-defined values for pH, $P_{CO_2}$, and $P_{O_2}$, and the calibration liquids thus prepared in the equipment and showing well-defined data are used for the calibration within the equipment, without being transferred to separate containers.

It would be of great interest to be able to perform the very calibration of the blood gas measuring equipment, especially semiautomatic equipment, using a handy reference liquid which may be produced and packed in suitable unit portions and distributed and stored with retention of its relevant data with high exactitude and reliability, in order that the calibration of the blood gas measuring equipment can be performed simply by introducing a unit portion or a part thereof in the equipment without the necessity of any special preparation or checking of the liquid.

DESCRIPTION OF THE INVENTION

Figure 1:
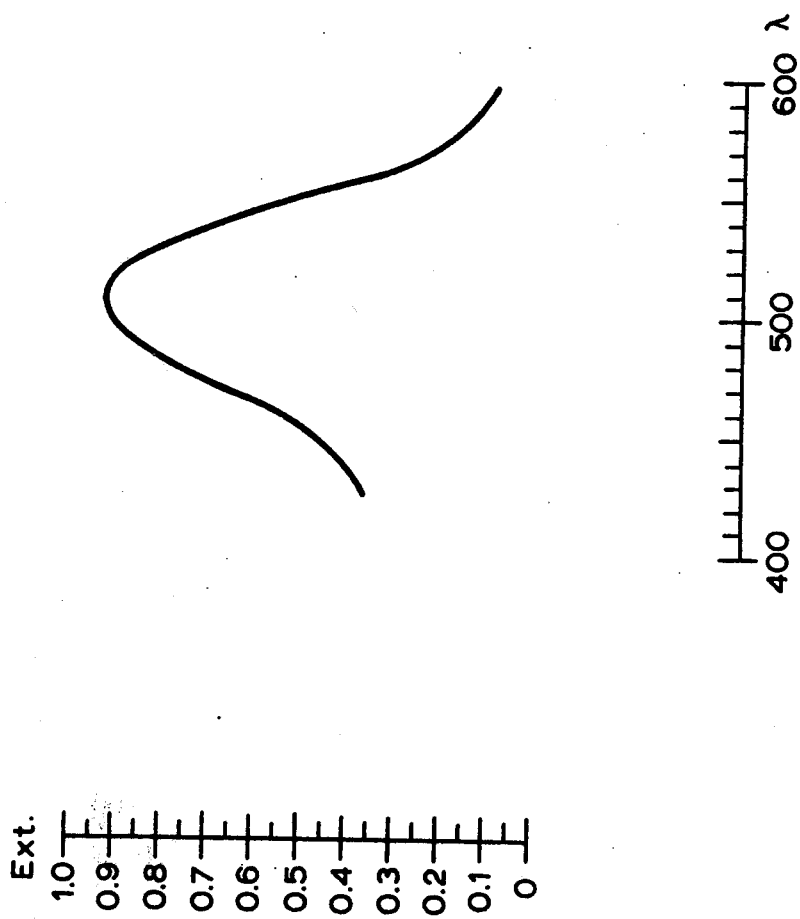
FIG. 1 is a curve showing the absorption of the dyestuff Ponseau 4R.

The present invention provides a package containing a reference liquid which may be used for quality control and/or calibration of blood gas measuring equipment, said reference liquid being known with respect to the parameters pH, $P_{CO_2}$, $P_{O_2}$, and, if desired, a parameter representing the hemoglobin concentration, the liquid being enclosed in a flexible, gas-tight container without the presence of any gas phase in the container, the total gas pressure in said liquid being at the most 600 mm Hg at 37° C.

The reference liquid enclosed in a flexible, and hence, self-collapsing, gas-tight container without the presence of any gas phase in the container constitutes a very practical unit portion which shows all the desired properties; such package is easy to handle and transport, and the reference liquid may, due to the flexible and self-collapsing character of the container, be transferred anaerobically to the blood gas analyzer more easily than with containerss of non-flexible character such as glass ampoules; for example, the flexible wall of the package may be pierced with a syringe needle and the liquid withdrawn anaerobically through the needle for injection into the blood gas analyzer. The principle of using flexible, gas-tight containers containing reference liquid is known from U.S. Pat. No. 3,681,255. However, as will be explained below, a reliable reference liquid package of this type is only obtained when it does not contain and will not during storage, manipulation, etc. contain any gas phase ("microbubbles" of gas) enclosed in the container together with the liquid. The present invention provides packages which solve this problem and which, for the first time, permit the safe and reliable utilization of flexible container-reference liquid unit portions for calibration and quality control of blood gas measuring equipment.

The presence and/or formation of microbubbles in reference liquids enclosed in gas-tight containers results in a drastic change of the data measured on the reference liquid, in particular the $P_{O_2}$. If, for example, a reference liquid in a flexible container shows a total gas pressure of 760 mm Hg at a certain temperature, and the barometric pressure at some stage during storage decreases to 700 mm Hg at the same temperature, a gas phase ("microbubbles" of a volume constituting about 0.1% of the volume of the liquid will be formed. Already the formation of such small proportion as 0.1% by volume of microbubbles will result in a 6% reduction of the $P_{O_2}$ value of the liquid phase, rendering the reference liquid useless as a standard or control liquid for the $P_{O_2}$ system of a blood gas analyzer. Microbubbles once formed will, of course, have a tendency to become redissolved in the liquid when the exterior conditions change to higher pressure, but even when the physicochemical equilibrium favours the redissolution of the gas phase, such redissolution may in practice be very slow, and total redissolution may not have occurred at the time when the portion is to be used. On the other hand, as the flexible container usually comprises a metal foil such as an aluminum foil, it is not transparent, and hence, it is not possible to ascertain, visually or by any other non-invasive method, whether or not microbubbles are in fact present. Consequently, at the time of use of the unit portion of reference liquid it cannot be taken for granted that its data are reliable, as storage and transportation conditions, for example, air freight transportation conditions, could easily involve situations where the external pressure would be so low that microbubbles would be formed in a flexible container filled, for example, with a reference liquid equilibrated at 37° C. and a barometric pressure of 758 mm Hg as disclosed in the above-mentioned U.S. Pat. No. 3,681,255.

According to the present invention, the total gas pressure in the reference liquid enclosed in the gas-tight container is at the most 600 mm Hg at 37° C., and this obviates the danger of formation of microbubbles under all such conditions to which the reference liquid packages can be subjected under normal or even relatively careless storage and transportation, thus providing a fully reliable unit portion reference liquid package offering all the advantages of the flexible, pierceable containers with respect to easy and safe manipulation without any required preconditioning by the end user.

It is preferred that the total gas pressure in the reference liquid in the package of the present invention is less than 550 mm Hg at 37° C.

As will be explained below, the final stage in the preparation of the reference liquid is normally an equilibration of a buffer liquid with a gas mixture which contains an inert gas, usually nitrogen, together with carbon dioxide and oxygen. During the equilibration, the partial pressures of oxygen and carbon dioxide are maintained at preselected desired values. The desired low total gas pressure in the liquid of less than 600 mm Hg at 37° C. is obtained by maintaining controlled subatmospheric conditions during the equilibration. Normally, the equilibration will be performed at 37° C. (the temperature at which the reference liquid is normally to be used in the blood gas analyzer), but it is also possible to perform the equilibration at temperatures differing from 37° C. and predetermine the partial gas pressures of carbon dioxide and oxygen to be used, in accordance with well-known physico-chemical principles and empirical corrections. Subsequent to the equilibration, the equilibrated liquid should be transferred to the flexible containers under gas-tight conditions and without contact with any gas phase in order to avoid any change in the parameters established in the equilibration.

The establishment of suitable pH and $P_{CO_2}$ buffer mixtures pertains to the known art. In principle, one may, in establishing such buffer solutions, utilize the well-known relationship between carbon dioxide dissolved in water and the pH of the solution:

$$pH = pK_A - m\sqrt{\mu} + \log\frac{[HCO_3^-]}{[CO_2]} \quad \text{(a modified Henderson-Hasselbalch equation)}$$

wherein $pK_A$ is the thermodynamic dissociation exponent of carbonic acid, $m$ is a constant, $\mu$ is the ionic strength, $[HCO_3^-]$ is the molar concentration of hydrogen carbonate ion, and $[CO_2]$ is the molar concentration of carbon dioxide.

It will thus be seen that the pH of a hydrogen carbonate/carbon dioxide solution is defined and known when the hydrogen carbonate and carbon dioxide concentrations are known. Such systems containing known concentrations of hydrogen carbonate ion and carbon dioxide may be established in various manners, e.g. by equilibrating a sodium hydrogen carbonate solution with a $CO_2$-containing gas of known partial pressure of $CO_2$, but it is also possible to start from sodium carbonate and form sodium hydrogen carbonate in situ by "titration" with the carbon dioxide, and according to a not preferred principle, it is possible to establish a solution with known hydrogen carbonate ion concentration and known carbon dioxide concentration by adding an acid, such as HCl, to a hydrogen carbonate solution or a carbonate solution.

The partial pressure of carbon dioxide in a liquid depends on the concentration of dissolved carbon dioxide in the liquid and of the solubility of carbon dioxide in the liquid in question, in the following manner:

$$[CO_2]_l = k_l \cdot P_{CO_2}$$

wherein $k_t$ is representative of the solubility of carbon dioxide in the liquid, which solubility is temperature-dependent. A liquid containing a hydrogen carbonate ion-carbon dioxide buffer system (as shown by the above Henderson-Hasselbalch equation) will, hence, show a fixed $P_{CO_2}$ at a fixed pH.

According to the invention, the hydrogen carbonate ion-carbon dioxide buffer system is preferably combined with another pH buffer system, according to the invention suitably a phosphate buffer system. Through this, the total buffer effect is increased with respect to the variation of both pH and $P_{CO_2}$ at loss or gain of small amounts of carbon dioxide. Hence, preferred reference liquids according to the invention contain both a phosphate buffer system and a hydrogen carbonate ion-carbon dioxide buffer system. In analogy with the above explanation, the establishment of these systems may be obtained in various manners, e.g. by equilibration of a phosphate buffer system with carbon dioxide, by equilibration of a phosphate/carbonate buffer system with $CO_2$. These various methods for establishing such buffer systems also pertain to the known art.

When the reference liquid according to the invention contains a coloring component which is to "simulate" hemoglobin and permit the use of the reference liquid for quality control and/or calibration of the hemoglobin measuring part of the blood measuring equipment, the coloring component is preferably one having an absorption maximum at or around an isobestic point of the system hemoglobin/hemoglobin-oxygen-complex (Hb/HbO$_2$), i.e. the point in which the molar extinction caused by Hb has the same size as the molar extinction caused by HbO$_2$, as blood gas measuring equipment comprising a hemoglobin measuring part is usually equipped with such filters that the absorption of the sample introduced is measured at or in a narrow range around one of the isobestic points, e.g. the points at 505 nm. Hence, dyestuffs having absorption maximum around 500 nm are suitable for use in the reference liquid according to the invention. As examples of such dyestuffs may be mentioned Amaranth, Allura Red and Ponceau 4 R, 70%. The last-mentioned dyestuff is a chemical azo dyestuff having C.I. No. 16,255 (1956). The compound is the trisodium salt of 1-(4-sulfo-1-naphthyl-azo)-2-naphthol-6,8-disulfonic acid. The dyestuff used should suitably be contained in the liquid in such concentration that it corresponds to the extinction of human blood, which, for Ponceau 4 R, 70% means a concentration of about 1.7 g/liter, and for Amaranth (the preferred dyestuff because of its stability) means a concentration of about 2 g/liter. FIG. 1 shows the absorption curve of Ponceau 4 R. Preferably, the reference liquid contains suitable preservatives for protection against microbial growth, for example, 2-phenylethanol and phenylmercuric nitrate.

The flexible, gas-tight container used for the package of the present invention is preferably a bag of a plastic-laminated metal foil. A suitable metal foil is an aluminum foil of a sufficient thickness to obviate the danger of pin holes, for example of a thickness of at least 20$\mu$, suitably a thickness of about 30$\mu$. Such metal foil without pin holes is gas-tight. The exterior side of the metal foil may be laminated with a plastic foil which protects against scratching etc., for example a polyester film of a thickness of 10–20$\mu$. The interior side of the metal foil is laminated with a plastic of low gas permeability and, as the closing of the bags is performed by welding the interior plastic layer, good weldability.

The properties of the plastic foil laminated to the interior of the metal foil are decisive to the performance of the packages of the present invention. Suitable plastics of low gas permeability are plastics having a permeability coefficient $E_1$ of less than 0.1 and preferably at the most 0.05. The permeability coefficient $$E_1 \left( \frac{cm^3 \times cm \times 10^{-10}}{cm^2 \times sec. \times cm\ Hg} \right)$$

for some typical low-permeability plastics appears from the below table:

| $E_1$ | Plastic |
|---|---|
| 0.003 | LPT - Low-permeable thermoplast (ICI) |
| 0.005 | polyvinylidene chloride (saran) |
| 0.01 | PAN C (polyacrylonitrile-copolymer, Barex 210) |
| 0.02–3 | polyethylene terephthalate (mylar) (terylene) |
| 0.02–3 | PVF - polyvinylfluoride |
| 0.05 | PA 6 - polyamide-6 (nylon-6) |
| 0.1 | PVC - polyvinylchloride |
| 0.9 | polyethylene |

As will be seen from the above, polyethylene has a permeability which is one order of magnitude higher than the most permeable of the other plastics mentioned, polyvinylchloride. According to the present invention it is preferred that the plastic foil used as a lining for the metal foil in the flexible containers has a permeability coefficient $E_1$ of at the most 0.1. In principle, LPT or polyvinylidene chloride showing the lowest permeability coefficient would be the most preferred materials for the interior lining, but from the point of view of the optimum combination of low permeability and good weldability, PAN C (polyacrylonitrile-copolymer, Barex TM 210) is the preferred plastic for the interior lining. Barex TM 210 is obtainable from Lonza AG, 4002 Basel, and is described as a copolymer of a high proportion of acrylonitrile (about 72 percent by weight) with a low proportion of other monomers. Barex TM 210 is thermoelastically workable up to a temperature of about 150° C. Above 150° C., it is entirely thermoplastic. Further details about Barex TM 210 are given in Verpackungs-Rundschau 1/1976, pages 90–92.

The thickness of the interior plastic lining in the container used according to the invention is suitably 20–80$\mu$, preferably about 50$\mu$.

Figure 2:
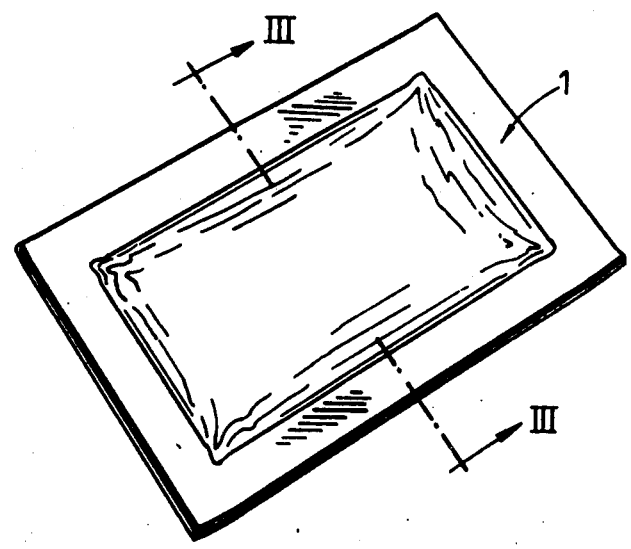
FIG. 2 is a plan view of one embodiment of a package according to the invention.

A suitable embodiment of a package according to the invention is shown in the drawing. FIG. 2 shows the exterior appearance of a preferred package according to the invention, and FIG. 3 shows a section along lines III—III of FIG. 2.

The package shown in FIG. 2 will normally have a size of about 4–7 cm. by 6–10 cm., and the volume of the liquid contained in the package will normally be a few milliliters, for example 1–10 ml, usually 3–7 ml, e.g. about 5 ml. The amount of liquid required for calibration or quality control of blood gas analyzers is often of the order of about 1.5 ml and at the least about 0.5 ml.

Figure 3:
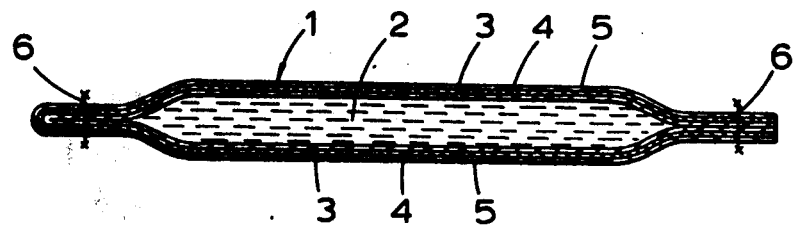
FIG. 3 is a cross-sectional view along the line III—III of FIG. 2.

In FIG. 3, the reference liquid 2 is gas-tightly and without any gas phase enclosed in a bag constituted by layers 3, 4 and 5 laminated together and closed at the edge side by welding the interior layer 5 along a welding seam 6. As will be seen from the drawing, also the opposite side of the bag relative to the edge side is also suitably compressed and welded along a welding seam 5, this being in order to obtain an easily handled form of the package. In principle, it would not be necessary for the function of the package as a gas-tight package to perform any welding at the non-edge side. The interior layer 3 of the laminate consists of a low-permeability plastic, preferably Barex TM 210, and has a thickness of about 50μ. The layer 4 is a pin-hole free aluminum foil of a thickness of about 30μ. If desired, an extra layer of plastic may be laminated between the aluminum foil and the Barex TM 210. Such extra layer may for example consist of polyamide-6 (nylon-6) and function as a binder layer between the aluminum foil and the Barex. In practice it has been found that the compatibility between the Barex TM 210 and the aluminum foil is satisfactory and that, hence, such extra binder laminate layer is not necessary. If a binder layer of for example nylon-6 is used between the aluminum foil and the Barex TM 210, the thickness of the binder layer is suitably about 12μ. In practice, it is generally not necessary to use such extra layer as the cohesion and compatibility between the aluminum foil and the Barex TM 210 is usually satisfactory.

The layer 5 is an optional protective layer, for example a 12μ polyester layer.

The invention also provides a process for preparing a reference liquid package as disclosed above. Said process comprises equilibrating a buffer liquid with a gas mixture containing carbon dioxide, oxygen, and an inert gas, the total gas pressure at the equilibration being at the most 600 mm Hg at 37° C., and thereafter transferring the equilibrated liquid gas-tightly and without contact with any gas phase into flexible, gas-tight containers without the presence of any gas phase in the containers.

The above process constitutes the preferred method of making the packages according to the invention. It would, in principle, also be possible to perform an equilibration with a gas mixture not containing $CO_2$ and thereafter generate the desired amount of $CO_2$ in situ by addition of an acid at a later stage, taking into account that the total gas pressure should be at the most 600 mm Hg at 37° C., but such alternative procedure is not preferred.

In the process according to the invention, the final adjustment of the parameters of the reference liquid is obtained in the equilibration stage. The equilibration is suitably performed in an equilibration tank, for example for equilibration of 50–60 liters of liquid, the tank being a thermostated tank with gas jets and having a total volume which is suitably 50–100% larger than the volume of the liquid to be equilibrated. The thermostating is suitably performed at 37° C. ± 0.1° C., and agitation (suitably by forcing the liquid through jets) and gas dosing may be performed in a manner so as to ensure a relatively fast equilibration, for example an equilibration time of about 16 hours (over night). The equilibration is performed with a gas mixture of exactly adjusted and known partial pressures of $CO_2$ and $O_2$, the gas mixture being suitably prepared in a manner known per se using a $CO_2$ gas supply, an $O_2$ gas supply, an $N_2$ gas supply, a pre-moistener and a pressure regulating unit permitting maintaining a constant subatmospheric pressure. The transfer of the equilibrated liquid into the containers used in the packages of the invention is, as mentioned above, performed gas-tightly, that is, anaerobically, and without contact with any gas phase. In this way, the parameters once established in the equilibration will not change during the transfer operations. Suitably, the transfer is performed by withdrawing the equilibrated liquid from the bottom of the equilibration tank, leaving a sufficient amount of the top layers of the liquid in the tank to ensure that the parameters in the liquid withdrawn will not undergo any change due to possible alterations in the partial pressures during the emptying of the equilibration tank. Of course, the withdrawal of the liquid should be performed sufficiently slowly to avoid mixing of upper and lower phases in the equilibration tank.

In practice, it is often preferred to transfer the equilibrated liquid from the equilibration tank to a storage container of the same flexible type as the end use containers, but with a large volume, for example 30 liters. Such storage tank may be constructed of the same materials as the bags described above. Prior to the transfer of the equilibrated liquid to the storage tank, the storage tank is carefully flushed with an inert gas such as nitrogen and thereafter totally evacuated so that the requirement concerning anaerobic and gas-phase free transfer of the liquid is met. As the operations following the equilibration are performed anaerobically and without contact with any gas phase, it is not necessary to perform these operations at any controlled temperature or pressure conditions, and the operations are normally performed at ambient temperature and the prevailing atmospheric pressure.

From the storage tank (or, if desired, directly from the equilibration tank), the equilibrated liquid is filled into laminated bags of the type described above. This transfer is performed gas-tightly and without contact with any gas phase, and a suitable operation is a bag-filling machine of the type which forms a web or band of the laminate into a tube, fills the tube with liquid and continuously seals the tube along transversily extending seams so as to form a strip of the pillow-shaped bags. Machines of this type are well-known in the packaging art.

The buffer liquid subjected to equilibration in the manner described above is, according to a most important aspect of the present invention, an aqueous pH-buffer solution containing an alkali hydrogen carbonate and an additional pH buffer system, preferably a phosphate buffer system. Such solution is suitably prepared by weighing out exact amounts of hydrogen carbonate and alkali phosphates and dissolving these in an exactly measured amount of deionized water together with the preservatives to be used.

As an alternative to the use of preservatives, the reference liquid packages may be subjected to sterilization by radioactive radiation.

The reference liquid packages prepared in this manner should be carefully checked by taking out samples at suitable intervals and measuring these samples by means of $P_{CO_2}/P_{O_2}$ measuring apparatus, pH equipment and, when applicable, Hb equipment.

According to a special aspect of the present invention, the reference liquid in the packages according to the invention additionally comprises oxygen reversibly contained in a dispersed organic substance. This aspect is discussed below.

REFERENCE LIQUIDS WITH INCREASED OXYGEN BUFFER CAPACITY.

According to this aspect of the invention, the reference liquid comprises oxygen reversibly contained in a dispersed organic substance which, per volume unit, is able to take up larger amount of oxygen than is water, in order to increase the $O_2$ capacity. This results in an increased "oxygen buffer capacity, so that any loss or gain of oxygen which may arise during manipulation and measurement, will result in a relatively small change in the $P_{O_2}$ value of the solution, this being the parameter with respect to which the $P_{O_2}$ part of the equipment is to be checked and/or calibrated.

The term "dispersed organic substance" is intended to comprise both organic substance which is so finely dispersed that a genuine or colloidal solution of the organic substance in the (usually predominantly aqueous) liquid is obtained, and organic substance in emulsion or in suspension in the predominantly aqueous liquid. This meaning may also be expressed by the term "dispersed" covering, in the present context, the three concepts of "dissolved", "emulsified", and "suspended".

The term "reversibly contained" is intended to describe that the oxygen is present in the organic substance in such a manner that the organic substance is able to deliver or take up oxygen under the manipulation and measuring conditions, so that the organic substance will, due to its ability to contain larger amounts of oxygen per volume unit than water, increase the oxygen buffer capacity of the reference liquid. The term "reversibly contained" may comprise both such cases in which the oxygen is dissolved or otherwise predominantly physically bound in the organic substance, and such cases where the oxygen is predominantly chemically bound, especially complex bound, to or in the organic substance in question. Non-water soluble organic materials showing a great soluting power for oxygen, are e.g. oils or oily synthetic organic substances and organic polymers. As examples may be mentioned silicone oils and silicone rubbers and fluorocarbon compounds, i.e. fluorinated, especially perfluorinated, hydrocarbons and compounds containing such fluorinated hydrocarbon groups, as well as polymers thereof. With such non-water soluble organic compounds which are liquids of lipoid character or solid substances, dispersions may be prepared which are emulsions of lipoid-in-water-type or suspensions. For the purpose of the present invention, such systems show the advantage that the great oxygen-soluting power of the lipoids or solids results in a large oxygen buffer capacity, whereas the liquid still retains its property as aqueous solution and hence, still permits the establishment of a $P_{CO_2}/pH$ buffer system. Of course, it is also possible to use combinations of water soluble and non-water soluble organic substances with large capacity for taking up oxygen.

As an illustration of the increase in solubility for oxygen which is obtained by using one of the substances mentioned, water soluble or non-water soluble, it may be mentioned that the solubility of $O_2$ (at 1 atmosphere's oxygen pressure and 25° C.) in water is 2.4% v/v, while it is 12% v/v in olive oil, typically 50% v/v in fluorocarbon compounds, typically 18% v/v in silicone rubbers, and typically 20% v/v in silicone oils.

Figure 4:
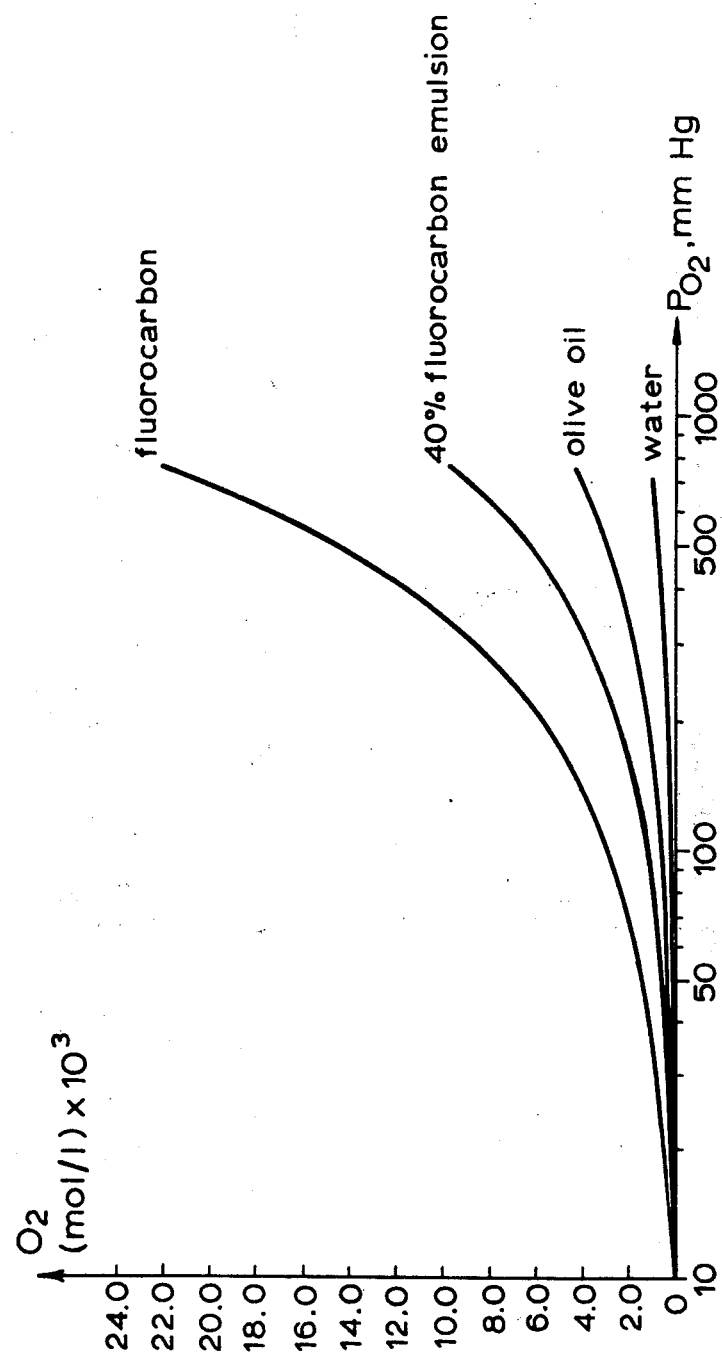
FIG. 4 is a graphical representation showing the molar amount of dissolved oxygen as a function of the partial pressure of oxygen for a number of reference liquids according to the invention.

The amount of dissolved oxygen in various systems as function of the partial pressure of oxygen (single logarithmical plot) is shown in FIG. 4 in which "fluorocarbon" designates perfluorotributylamine. It will be noted that while even a very small change in the oxygen amount in pure water will result in a very large difference in $P_{O_2}$, a change of the oxygen amount in, e.g., the fluorocarbon compound will result in a far smaller change in $P_{O_2}$, and that, e.g., a 40% emulsion of the fluorocarbon compound in water shows a far better oxygen buffer capacity than water, i.e., shows far less $P_{O_2}$ change at a given change in oxygen content.

When the reference liquid according to the invention is an emulsion or suspension, it is preferred that the emulsified or suspended phase constitutes at the most 60% of the total volume, especially 20–50%, as the water phase should of course be of a sufficient proportion so as to avoid a decrease in the quality of the pH measurement. Hence, it is clear that in composing the liquid according to the invention, one will preferably choose such emulsified or suspended components which show an especially high solubility for oxygen, e.g. the above-mentioned fluorocarbon compounds.

As examples of fluorohydrocarbons and fluorohydrocarbon group-containing compounds, in other words fluorocarbon compounds, which are useful for the purpose of the present invention may be mentioned perfluorotributyl amine $((C_4F_3)_3N)$ which is sold by 3M Company under the designation "FC 43", perfluoromethyl cyclohexane and perfluorodimethyl decaline.

Because of its good emulsifying properties and high ability of dissolving oxygen, perfluorotributyl amine is a preferred compound. As an example of a silicone oil useful as emulsified phase in the reference liquid according to the invention may be mentioned Dow Corning "200 Silicone Oil", and as an example of a silicone rubber useful as suspended phase in the reference liquid according to the invention may be mentioned silicone rubber CAF4/60 Rhodorsil, Rhône Poulenc, Paris.

To obtain a stable emulsion or suspension it may be necessary that the reference liquid according to the invention contains a suitable emulsifying or suspending agent, and this agent may be of any type which does not adversely influence the parameters to be determined by means of the reference liquid, and which gives a stable emulsion or suspension of the organic material selected. Suitable emulsifiers or suspending agents for this purpose are commercially available. As an example of an emulsifier which has been found to be suitable in the preparation of emulsions of fluorohydrocarbons in water for the purpose of the present invention may be mentioned Pluriol PE 6800, BASF (polyoxy propylene polyoxy ethylene).

As mentioned above, the organic substance in which the oxygen in the reference liquid according to the invention is reversibly contained may be a substance to which oxygen is reversibly chemically bound, especially complex-bound.

Most chemical processes involving oxygen are characteristic in that the processes are substantially irreversible, so that an oxygen-containing compound once formed will not to any substantial degree be able to liberate oxygen or, expressed in another manner, the oxygen-containing compounds formed by the irreversible processes are not suitable for increasing the oxygen buffer capacity of the reference liquids according to the present invention.

Reversible oxygen processes do exist, e.g. in the blood hemoglobin molecule, which is able to reversibly take up and give off oxygen in substantial amounts, and which therefore in principle would be excellently suitable for the purpose of the present invention. However, outside the organism, the hemoglobin molecule is relatively unstable, and therefore not suitable for the purpose of the present invention.

However, other — and simpler and less sensible — organic compounds than the hemoglobin molecule are known which are able to reversibly complex-bind oxygen. As examples may especially be mentioned metal organic compounds of transition group metals, especially cobalt or iron, in which the metal is bound, usually complex-bound, to nitrogen-containing groups, e.g. transition group metal complexes with porfyrine-like compounds such as iron(II)phthalocyanine tetrasulfonic acid.

For the purpose of the present invention, the organic substance which is able to chemically bind, especially complex-bind, oxygen reversibly should preferably be one which has a suitable position of the equilibrium of the reversible oxygen reaction in question, i.e. a position of the equilibrium which resembles that of hemoglobin (the greatest resemblance with authentic blood), and/or a position of the equilibrium which results in an optimum oxygen buffer capacity at or about the $P_{O_2}$ value which is to be possessed by the $P_{O_2}$ of the reference liquid.

With respect to the position of the equilibrium of the oxygen reaction of hemoglobin, the following applies when the oxygen uptake of the blood is considered in a simplified manner:

$$Hb + O_2 \rightleftarrows HbO_2$$

wherein Hb is the hemoglobin molecule, $O_2$ is the oxygen molecule, and $HbO_2$ is the oxygen-containing hemoglobin complex.

The solubility of oxygen (in free form) in the water phase of blood can reasonably be put at $1.4 \cdot 10^{-6}$ mole of oxygen per liter per mm Hg oxygen partial pressure. Empirically, at an oxygen partial pressure of 27 mm Hg, equal amounts of on one hand hemoglobin on the Hb form and on the other hand hemoglobin on $HbO_2$ form are present in the blood. At this partial pressure, the concentration of dissolved oxygen in the water phase of blood is:

$$[O_2] = 1.4 \cdot 10^{-6} \cdot 27 \sim 3.8 \cdot 10^{-5}.$$

The stability constant K for the oxygen-containing hemoglobin complex is $$K = \frac{[HbO_2]}{[Hb][O_2]}$$

and as (vide above) $[HbO_2] = [Hb]$ at $[O_2] \sim 3.8 \cdot 10^{-5}$, the following applies:

$$K = \frac{1}{3.8 \cdot 10^{-5}} \sim K = 10^{4.5}$$

From this follows that among the oxygen complex-forming organic compounds binding oxygen in the same manner as hemoglobin, i.e. according to the above reaction scheme, the ideal compounds for use as oxygen buffers in a reference liquid which is very close to the properties of blood in this regard will be such compounds, for which the stability constant of their oxygen complex is about $10^{4.5}$, e.g. in the range of $10^3 - 10^{5.5}$, especially $10^4 - 10^5$.

Another type of (different from hemoglobin) organic compounds which reversibly form complex with oxygen, bind oxygen according to the reaction scheme:

$$2L + O_2 \rightleftarrows L-O_2-L$$

wheren L is the ligand which is able to bind oxygen, and $L-O_2-L$ is the complex compound in its oxygenated form.

The stability constant of the above-mentioned oxygenated complex compound $L-O_2-L$ is $$K = \frac{[L-O_2-L]}{[L]^2[O_2]}$$

wherein $[O_2]$ is a concentration of oxygen (in free form) dissolved in the system in question.

Decisive to the suitability of the oxygen complex-forming compound for use in the liquid according to the invention is that around the oxygen partial pressure which the reference liquid is to possess, a suitable oxygen buffer capacity should be obtained, which means that any loss of small amounts of oxygen from the liquid, or any gain of small amounts of oxygen to the liquid, e.g. during the manipulation of the liquid and during a calibration operation, should result in as small a change in the $P_{O_2}$ liquid as possible. A high oxygen buffer capacity is of course in principle obtained when the concentration of the oxygen complex-forming compound in the reference liquid is high, but the oxygen partial pressure around which the buffer effect has its optimum depends on both the concentration mentioned and on the size of the above-mentioned stability constant K. When composing a reference liquid according to the invention using an oxygen complex-forming compound, one should, therefore, as oxygen complex-forming compound preferably select such compound in such concentration that optimum oxygen buffer capacity is obtained around the oxygen partial pressure to be possessed by the reference liquid.

For complex compounds binding oxygen according to the reaction scheme $2L + O_2 \rightarrow L - O - L$, there may be calculated, as examples, suitable stability constants for oxygen complexes for use in reference liquids, the oxygen partial pressure of which is to be at one of the three values at which it is often desired to calibrate, i.e. 500 mm Hg, 150 mm Hg, and 50 mm Hg. For these, the following is true:

(1) $[O_2] = 6 \cdot 10^{-4}$ mol/liter ($\sim$500 mm Hg)

(2) $[O_2] = 2 \cdot 10^{-4}$ mol/liter ($\sim$150 mm Hg)

(3) $[O_2] = 6 \cdot 10^{-5}$ mol/liter ($\sim$50 mm Hg)

If it is desired to use the ligand in these cases in a concentration of $10^{-1}$ mol/liter, the following values are calculated for the stability constant K which at the three $[O_2]$ values mentioned gives maximum oxygen buffer capacity:

$$K_1 = \frac{0.603}{10^{-1} \cdot 6 \cdot 10^{-4}} = 10^4$$

$$K_2 = \frac{0.603}{10^{-1} \cdot 2 \cdot 10^{-4}} = 3 \times 10^4$$

$$K_3 = \frac{0.603}{10^{-1} \cdot 6 \cdot 10^{-5}} = 10^5$$

Figure 5:
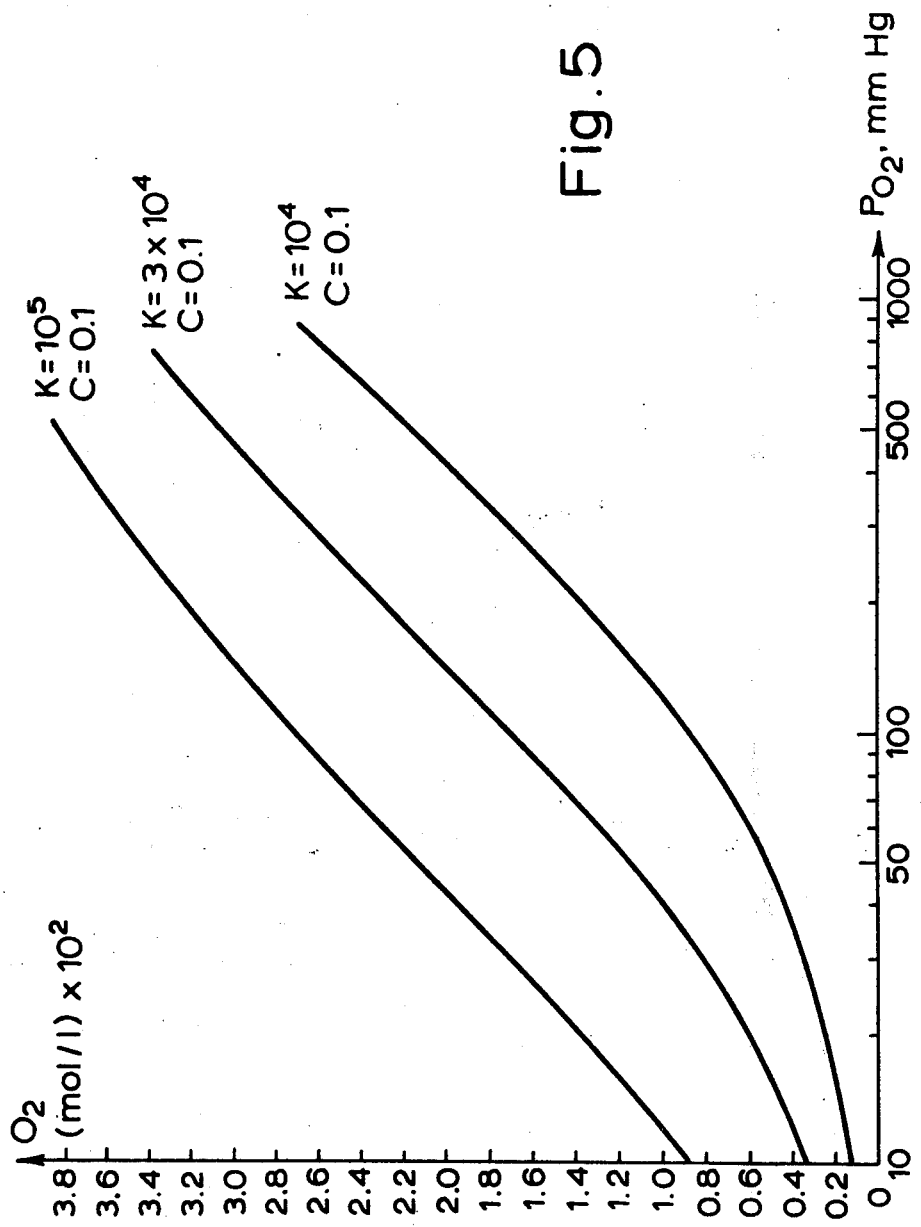
FIG. 5 is a logarithmic plot of the oxygen content of reference liquids according to the invention as a function of the partial pressure of oxygen.

FIG. 5 shows, as a single logarithmic plot, the concentration of total oxygen amount as function of the partial pressure of oxygen for oxygen complexes with the three above-mentioned stability constants, each of them in a concentration of $10^{-1}$ mol/liter in the reference liquid. It will be seen how the oxygen complex compounds show a considerable oxygen buffer capacity (considerably greater steepness of the graph than for $H_2O$) in a broad range around the partial pressures mentioned, so that loss or gain of a certain amount of oxygen in the range stated will result in percent-wise the same (relatively small) change in the oxygen partial pressure of the system.

On the background of the examples given above and FIG. 2 it can be stated that also for complex compounds binding oxygen according to the reaction sceheme $2L + O_2 \rightarrow L-O_2-L$, beneficial stability constants will be in the range of $10^3 - 10^{5.5}$, especially $10^4 - 10^5$.

When the reference liquid according to the invention contains, as oxygen buffer capacity-increasing organic substance, an oxygen complex-forming compound, the concentration of this compound is preferably between $10^{-4}$ and 1 mol per liter, especially from $10^{-3}$ to $5 \cdot 10^{-1}$ mol per liter.

When the reference liquid contains an "oxygen buffer system" of one of the above-described types, its equilibration and packaging may be performed in the same manner as described for reference liquids not containing such systems.

Embodiments of the invention are further described in the following examples.

EXAMPLE 1

Bicarbonate-containing phosphate buffer solution

The composition is:

| | | |
|---|---|---|
| $KH_2PO_4$ | 2.173 | g |
| $Na_2HPO_4 \cdot 2H_2O$ | 7.141 | g |
| $NaHCO_3$ | 1.273 | g |
| phenylmercuric nitrate | 0.01 | g |
| water | 989.5 | g |
| 2-phenylethanol | 2 | g |

At 37° C., a portion of solution of this composition is equilibrated with a $CO_2-O_2-N_2$ mixture having a partial pressure of $CO_2$ of 60 mm Hg and a partial pressure of $O_2$ of 39 mm Hg, the total pressure during the equilibration being 539 mm Hg. Upon equilibration, the resulting liquid is transferred, under gas-tight conditions and without contact with any gas phase, to a 30 liter storage tank consisting of a flexible bag made of Barex TM 210-aluminum foil-polyester laminate which has in advance been flushed with nitrogen and thereafter totally evacuated. From the storage tank, the liquid is transferred gas-tightly into Barex TM 210-aluminum foil-polyester bags formed by welding (heat-sealing), from a web or band of the same material, using a laminate bag filling/sealing machine. The resulting packages contain reference liquid showing a pH of 7.1, a $P_{CO_2}$ of 60 mm Hg, and a $P_{O_2}$ of 39 mm Hg, and are suitable as, for example, control liquid packages for determining the ability of a blood analyzer to accurately measure blood samples showing acidemia condition.

EXAMPLE 2

Bicarbonate-containing phosphate buffer solution

The composition is:

| | | |
|---|---|---|
| $KH_2PO_4$ | 1.585 | g |
| $Na_2HPO_4 \cdot 2H_2O$ | 8.99 | g |
| $NaHCO_3$ | 1.857 | g |
| phenylmercuric nitrate | 0.01 | g |
| Water | 988.2 | g |
| 2-phenylethanol | 2 | g |

In the same manner as described in Example 1, the solution is equilibrated at a total pressure of 539 mm Hg, the partial pressure of carbon dioxide being 40 mm Hg, and the partial pressure of oxygen being 93 mm Hg, and thereafter packed in laminate bags. The resulting packages are suitable as control liquid packages or calibration liquid packages for blood gas analyzers, the pH of the liquid being 7.39, the $P_{CO_2}$ of the liquid being 40 mm Hg, and the $P_{O_2}$ of the liquid being 93 mm Hg.

EXAMPLE 3

The same procedure and the same composition as described in Example 2 are used, with the exception that in the equilibration procedure, the partial pressure of carbon dioxide is 18 mm Hg, and the partial pressure of oxygen is 162 mm Hg. The pH of the equilibrated liquid is 7.6. The resulting packages are suitable as control liquid packages for blood gas analyzers to check the performance of the blood gas analyzers in connection with blood samples showing alkalemia conditions.

EXAMPLE 4

Bicarbonate-containing phosphate buffer solution

The composition of the aqueous solution is:

| In the water phase: | | |
|---|---|---|
| disodium hydrogen phosphate | 0.047 | molal |
| potassium dihydrogen phosphate | 0.012 | molal |
| sodium hydrogen carbonate | 0.022 | molal |
| Amaranth | 2 | g/liter |
| phenylmercuric nitrate | 0.01 | g/liter |
| 2-phenylethanol | 2 | g/liter |

This solution is equilibrated with a gas mixture having a partial pressure of $CO_2$ of 40 mm Hg and a partial pressure of $O_2$ of 70 mm Hg at a temperature of 37° C., the total gas pressure being 540 mm Hg, and the resulting equilibrated liquid is as tightly filled into laminated bags as described in Example 1. The resulting packages are suitable for calibration of blood gas analyzers, and show the following data at 37° C.: pH = 7.36, $P_{CO_2}$ = 40 mm Hg, $P_{O_2}$ = 70 mm Hg, and Hb = 15 g%.

EXAMPLE 5

A bicarbonate-containing phosphate buffer solution

The composition of the aqueous solution is:

| | | |
|---|---|---|
| disodium hydrogen phosphate | 0.022 | molal |
| potassium dihydrogen phosphate | 0.022 | molal |
| sodium hydrogen carbonate | 0.012 | molal |
| Amaranth | 1.5 | g/liter |
| Phenylmercuric nitrate | 0.01 | g/liter |
| 2-phenylethanol | 2 | g/liter |

This solution is equilibrated with a gas mixture having a partial pressure of $CO_2$ of 80 mm Hg and a partial pressure of $O_2$ of 150 mm Hg at a temperature of 37° C., the total gas pressure being 540 mm Hg, and the resulting equilibrated liquid is gas-tightly filled into laminate bags as described in Example 1. The resulting packages are suitable for calibration of blood gas analyzers, and show the following data at 37° C.: pH = 6.84, $P_{CO_2}$ = 80 mm Hg, $P_{O_2}$ = 150 mm Hg, and Hb = 10 g%.

EXAMPLE 6

A bicarbonate-containing phosphate buffer having a disperse phase of fluorohydrocarbon.

The aqueous phase of this liquid has the same composition as the buffer solution described in Example 4, except that it does not contain Amaranth.

This buffer solution constitutes 60% of the liquid, 40% being fluorohydrocarbon (perfluorotributyl amine) emulsified in the water phase.

The emulsion is equilibrated and filled into laminate bags in the same manner as in Example 4, and the resulting packages show the same data as the packages of Example 4 with respect to pH, $P_{CO_2}$ and $P_{O_2}$.

EXAMPLE 7

A bicarbonate-containing phosphate buffer with a disperse phase of fluorohydrocarbon.

The aqueous phase of this reference liquid has the same composition as the buffer solution of Example 5, except that it does not contain Amaranth.

This buffer solution constitutes 60% of the liquid, 40% being fluorohydrocarbon (perfluoromethyl cyclohexane) emulsified in the water phase.

The emulsion is equilibrated and filled into laminate bags in the same manner as in Example 5, and the resulting packages show the same data as the packages of Example 5 with respect to pH, $P_{CO_2}$ and $P_{O_2}$.

EXAMPLE 8

A bicarbonate-containing aqueous phosphate buffer solution having a content of iron-phthalocyanine tetrasulfonic acid The composition is:

| | | |
|---|---|---|
| disodium hydrogen phosphate | 0.022 | molal |
| potassium dihydrogen phosphate | 0.022 | molal |
| sodium hydrogen carbonate | 0.012 | molal |
| iron(II) phthalocyanine tetrasulfonic acid | 2% | |
| iron(II) phthalocyanine tetrasulfonic acid ($O_2$ complex) | 1% | |
| phenylmercuric nitrate | 0.01 | g/liter |
| 2-phenylethanol | 2 | g/liter |

This solution is equilibrated with a gas mixture having a partial pressure of $CO_2$ of 80 mm Hg and a partial pressure of $O_2$ of 1 mm Hg at a temperature of 37° C., the total gas pressure in the liquid being 540 mm Hg, and the resulting equilibrated liquid is gas-tightly filled into laminate bags as described in Example 1. The resulting packages are suitable for quality control of blood gas analyzers and show the following data at 37° C.: pH = 6.84, $P_{CO_2}$ = 80 mm Hg, $P_{O_2}$ = 1 mm Hg, and Hb = 0 g%.

EXAMPLE 9

A bicarbonate-containing phosphate buffer having a disperse phase of silicone rubber The composition is:

| | | |
|---|---|---|
| In the water phase: | | |
| disodium hydrogen phosphate | 0.047 | molal |
| potassium dihydrogen phosphate | 0.012 | molal |
| sodium hydrogen carbonate | 0.021 | molal |
| Ponceau 4 R | 1.7 | g/liter |

-continued

| | | |
|---|---|---|
| In the water phase: | | |
| phenylmercuric nitrate | 0.01 | g/liter |
| 2-phenyl ethanol | 2 | g/liter |

The water phase constitutes 80% of the liquid, the remaining 20% being finely dispersed silicone rubber particles (CAF4/60 "RHODORSIL").

This liquid is suitable for preparing packages of reference liquid having pH = 7.36, $P_{CO_2}$ = 40 mm Hg, $P_{O_2}$ = 70 mm Hg, and Hb = 14 g%, at 37° C., which is done by equilibrating the liquid with a gas mixture having a $CO_2$ partial pressure of 40 mm Hg and an $O_2$ partial pressure of 70 mm Hg at 37° C., the total gas pressure in the liquid being 540 mm Hg, and gas-tightly filling the resulting equilibrated liquid into laminate bags as described in Example 1.

We claim:

1. A package containing a synthetic reference liquid for quality control and/or calibration of blood gas measuring equipment, said liquid being enclosed in a flexible, gas-tight container without the presence of any gas phase in the container and showing (at a fixed temperature) a known pH, a known partial pressure of carbon dioxide and a known partial pressure of oxygen, the total gas pressure in said liquid being less than 600 mm Hg at 37° C.

2. A package as claimed in claim 1 wherein the total pressure of gases in the liquid is less than 550 mm Hg at 37° C.

3. A package as claimed in claim 1 wherein the reference liquid is an aqueous solution containing a hydrogen carbonate ion—carbon dioxide buffer system and a phosphate buffer system.

4. A package as claimed in claim 1 wherein the flexible, gas-tight container is a metal-plastic laminate bag.

5. A package as claimed in claim 4 wherein the metal is aluminum foil of a thickness of at least 20$\mu$, and the interior plastic laminate layer is a layer of a low-permeable plastic having a permeability coefficient $E_1$ of at the most 0.1.

6. A package as claimed in claim 5 wherein the low-permeability plastic layer is a 20-80$\mu$ layer of an acrylonitrile copolymer having a permeability coefficient $E_1$ of 0.01 and containing a proportion of acrylonitrile of about 72 percent by weight.

7. A package as claimed in claim 5 wherein the low-permeability plastic layer is a layer of polyvinylidene chloride having a permeability coefficient $E_1$ of 0.005.

8. A package as claimed in claim 5 wherein the outside of the aluminum foil is laminated with a 10-20$\mu$ polyester layer.

9. A package as claimed in claim 1 wherein the reference liquid contains a coloring component showing maximum or significant absorption at about 500 nm.

10. A package as claimed in claim 1 wherein the reference liquid contains oxygen reversibly contained in an emulsified or suspended non-water soluble organic substance selected from a silicone oil, a silicone rubber, a perfluorinated hydrocarbon compound, and a compound containing perfluorinated hydrocarbon groups.

11. A package as claimed in claim 10 wherein the emulsified or suspended phase constitutes 20 – 50% of the total volume.

12. A package as claimed in claim 10 wherein the reference liquid contains oxygen reversibly contained in perfluorotributyl amine.

13. A package as claimed in claim 1 wherein the reference liquid contains oxygen reversibly contained in an oxygen complex-forming organic substance in which the stability constant of the oxygen complex is in the range of $10^3 - 10^{5.5}$.

14. A process for preparing a package as claimed in claim 1 comprising equilibrating a buffer liquid with a gas mixture containing carbon dioxide oxygen, and an inert gas, the total gas pressure at equilibration being at the most 600 mm Hg at 37° C., and thereafter transferring the equilibrated liquid under gas-tight conditions and without contact with any gas phase into flexible, gas-tight containers without the presence of any gas phase in the containers.

* * * * *